US007065176B2

(12) United States Patent
Moermond et al.

(10) Patent No.: US 7,065,176 B2
(45) Date of Patent: Jun. 20, 2006

(54) METHOD AND SYSTEM TO INSPECT A COMPONENT

(75) Inventors: Kevin Moermond, Cincinnati, OH (US); Andy Joseph Galish, West Chester, OH (US); John Robert Brehm, Middletown, OH (US); Francis Howard Little, Cincinnati, OH (US); Dean Fredrich Graber, Hamilton, OH (US); Michael Timothy La Tulippe, Fairfield, OH (US); Ronald Cecil McFarland, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 137 days.

(21) Appl. No.: 10/250,010

(22) Filed: May 28, 2003

(65) Prior Publication Data

US 2004/0240607 A1    Dec. 2, 2004

(51) Int. Cl.
*G01B 15/06* (2006.01)
(52) U.S. Cl. ....................................................... 378/58
(58) Field of Classification Search ............ 378/57–63, 378/65, 205
See application file for complete search history.

(56) References Cited

U.S. PATENT DOCUMENTS

| 4,260,889 | A | * | 4/1981 | Osborn et al. ................. 378/61 |
| 5,119,408 | A |   | 6/1992 | Little et al. ..................... 378/4 |
| 5,778,043 | A | * | 7/1998 | Cosman ....................... 378/65 |
| 5,985,680 | A | * | 11/1999 | Singhal et al. .................. 438/7 |
| 6,459,760 | B1 |   | 10/2002 | D'Ambrosio ................. 378/43 |
| 2002/0181650 | A1 |   | 12/2002 | D'Ambrosio |

FOREIGN PATENT DOCUMENTS

| JP | 01299447 | 4/1989 |
| WO | WO 9954717 | 10/1999 |

* cited by examiner

*Primary Examiner*—Edward J. Glick
*Assistant Examiner*—Jurie Yun
(74) *Attorney, Agent, or Firm*—Charles L. Moore; Moore and Van Allen PLLC; V. G. Ramaswamy

(57) ABSTRACT

A system and method to inspect a component is disclosed. The system to inspect a component may include an x-ray source to direct an x-ray beam through the component and an x-ray detector to detect the x-ray beam after passing through the component. A processor may be included to transform coordinates on an x-ray detection panel of the x-ray detector that detect any defects to a digital representation of locations on the component of any defects.

32 Claims, 5 Drawing Sheets

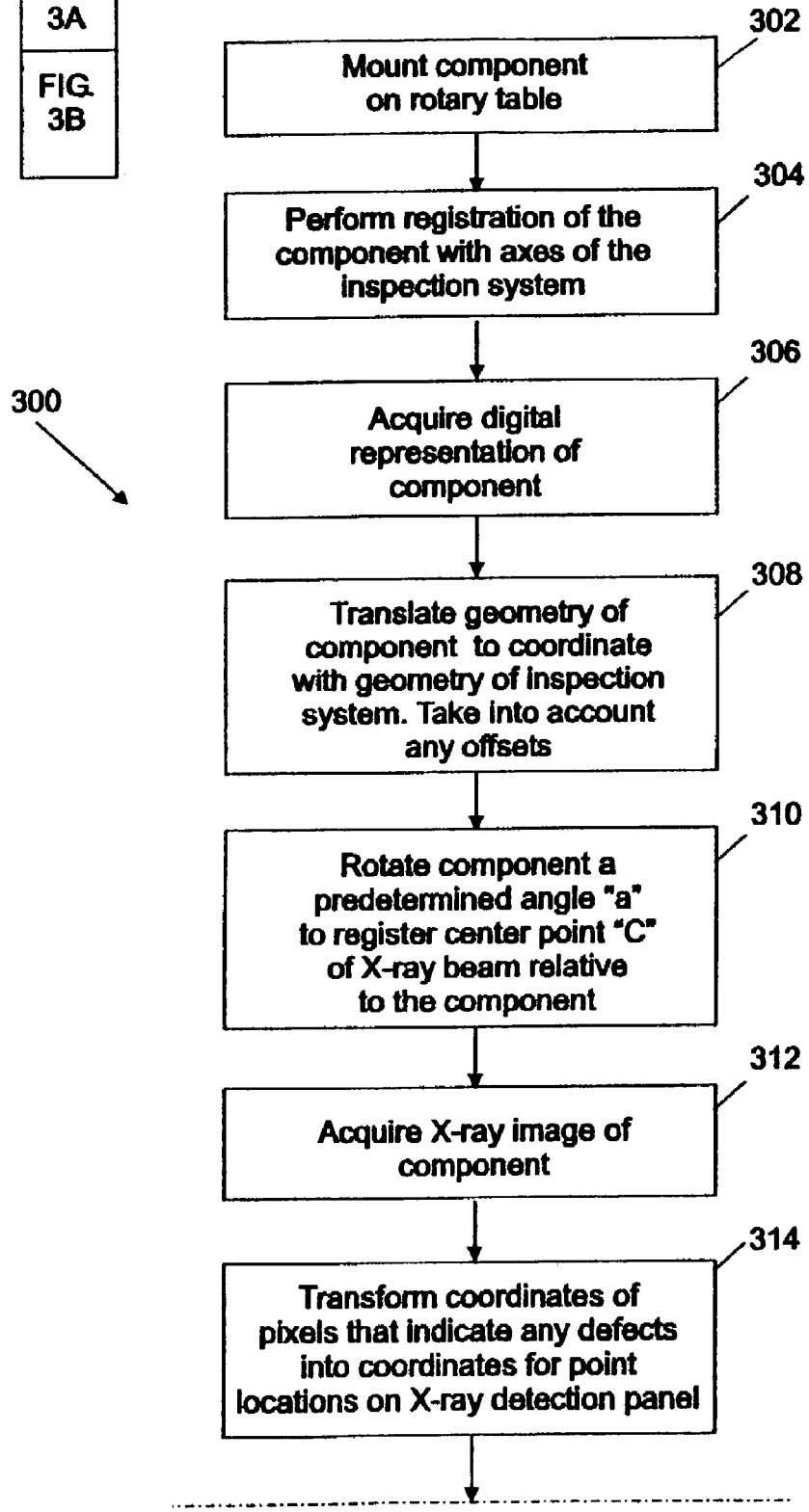

METHOD AND SYSTEM TO INSPECT A COMPONENT

BACKGROUND OF INVENTION

Field of the Invention

The present invention relates to inspection of workpieces, components or the like, and more particularly to an x-ray inspection system and method.

X-ray devices may be used to perform non-destructive testing or inspection of workpieces, components or other objects. The x-rays may be used to inspect welds or other features, particularly in large components. Flaws or defects can be easily detected using x-rays but location of the defect may not be easily determined from a two dimensional image of a three dimensional object.

Accordingly, there is a need to provide a method and system to inspect a component or object that can precisely identify the location of any flaws or defects. There is also a need to provide a method and system to inspect a component or object that may use a three dimensional digital representation of the component or object to locate the defect in relation to the component geometry. There is also a need to provide a method and system to inspect a component that may use the digital representation of the component to identify any defects and automatically mark the component to identify the location of the defects for subsequent repair or for other purposes.

SUMMARY OF INVENTION

In accordance with an embodiment of the present invention, a method to inspect a component may include transforming coordinates of pixels on an x-ray image of the component that indicate any defects in the component to coordinates in a digital representation of the component. The component may be marked using the coordinates in the digital representation to identify locations of any defects.

In accordance with another embodiment of the present invention, a method to inspect a component may include determining coordinates defining any defects in the component on an x-ray detection panel; and transforming the coordinates defining any defects on the x-ray detection panel to locations on the component.

In accordance with another embodiment of the present invention, a method to inspect a component may include transferring coordinates of pixels on an x-ray image of the component that indicate any defects in the component to coordinates of point locations on an x-ray detection panel. The point locations on the x-ray detection panel corresponding to any defects may be translated to coordinates for each point location of any defects in a digital representation of the component. A true location of each of each point on a surface of the component corresponding to any defect may be determined from an intersection of an x-ray beam with each point. A surface normal may be determined at each point on the surface of the component corresponding to any defect, and each point may be marked on the surface of the component corresponding to the location of any defects.

In accordance with another embodiment of the present invention, a system to inspect a component may include an x-ray source to direct an x-ray beam through the component. An x-ray detector may be included to detect the x-ray beam after passing through the component, wherein the x-ray detector may include an x-ray detection panel. A processor may be provided to transform coordinates on the x-ray detection panel that detect any defects to a digital representation of locations on the component of any defects.

In accordance with another embodiment of the present invention, a system to inspect a component may include an x-ray source to direct an x-ray beam through the component. An x-ray detector may be provided to detect the x-ray beam after passing through the component. A display may display an x-ray image of the component in response to passing the x-ray beam through the component. A digital representation of the component may also be provide and a processor. A data structure may operate on the processor to transform coordinates of pixels on the x-ray image of the component that indicate any defects to coordinates in the digital representation of the component. A marking device may be included to mark the component using the coordinates in the digital representation to identify locations of any defects.

BRIEF DESCRIPTION OF DRAWINGS

FIGS. 3A and 3B are a flow chart of a method of inspecting a component in accordance with an embodiment of the present invention.

DETAILED DESCRIPTION

The following detailed description of preferred embodiments refers to the accompanying drawings which illustrate specific embodiments of the invention. Other embodiments having different structures and operations do not depart from the scope of the present invention.

Figure 1:
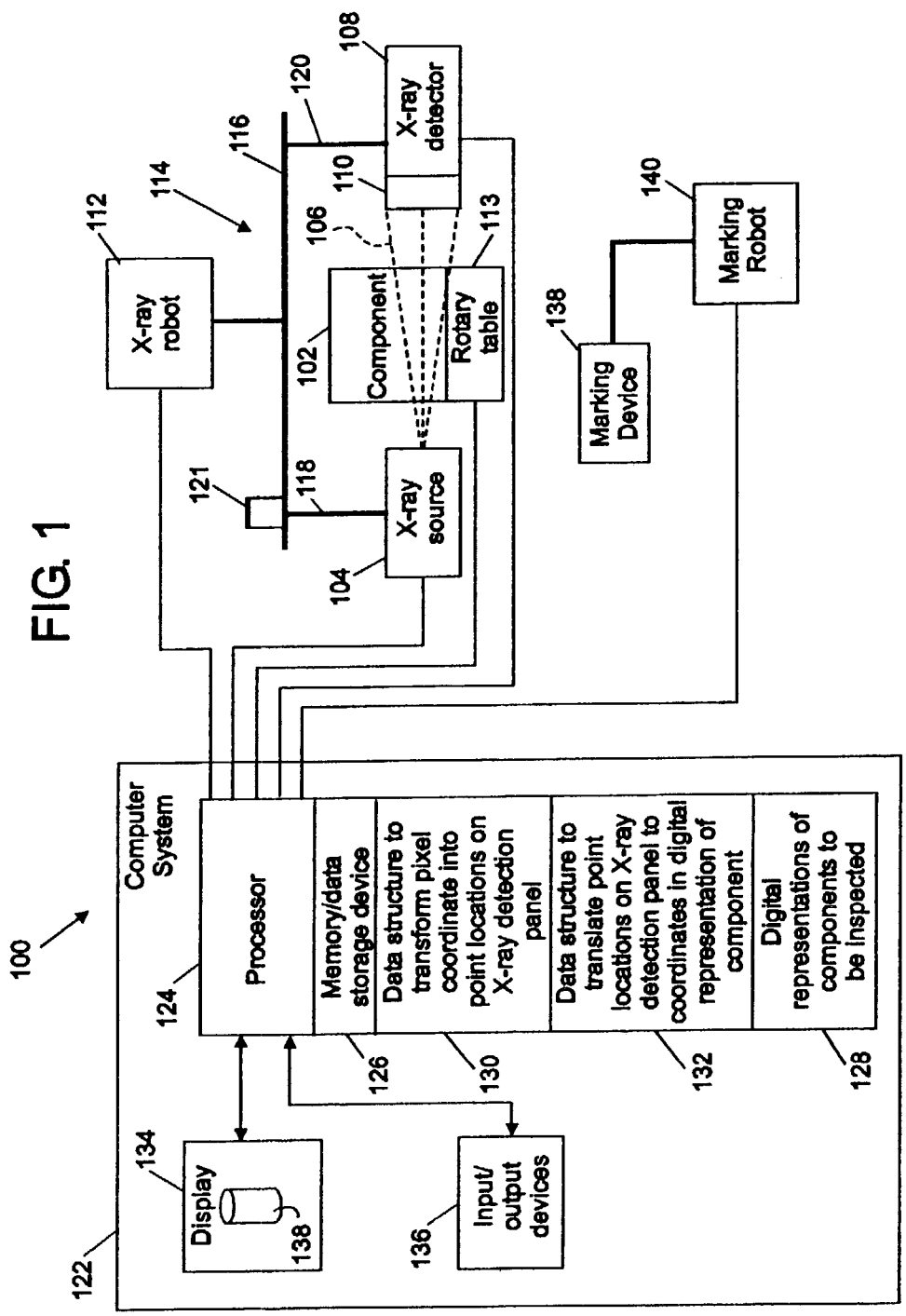
FIG. 1 is a block diagram of an example of a system to inspect a component in accordance with an embodiment of the present invention.

FIG. 1 is a block diagram of an example of a system 100 to inspect a component, such as component 102, in accordance with an embodiment of the present invention. The system 100 may include an x-ray source 104 to direct an x-ray beam 106 through the component 102 to inspect the component 102. An x-ray detector 108 may be provided to detect the x-ray beam 106 after passing through the component 102. The x-ray detector 108 may include an x-ray detection panel 110 to receive the x-ray beam 106. The x-ray source 104 and x-ray detector 108 may be mounted to a robot 112, manipulator or similar device. The component 102 may be mounted on a rotary table 113 or similar mechanism to hold and rotate the component 102 for inspection of different portions of the component 102 if the component 102 is too large to fit completely within the x-ray beam 106.

A slide bar assembly 114 or the like may be attached to the robot 112 or may be part of the robot 112. The slide bar assembly 114 may include a support assembly 116 or linear axis assembly and a first and second support arm 118 and 120 that may each be movably connected to the support assembly 116. The x-ray source 104 may be coupled to the first support arm 118 and the x-ray detector 108 may be coupled to the second support arm 120. The support assembly 116 may include a motorized mechanism 121 to move the x-ray source 104 and x-ray detector 108 toward or away from each other and the component 102 equal distances.

This may insure that a proper image of the component 102 may be viewed or acquired as part of the inspection.

The system 100 may also include a computer system 122 or the like. The computer system 122 may be connected to the x-ray robot 112, the rotary table 113, the x-ray source 104 and x-ray detector 108 to control their operation and the operation of the slide bar assembly 114. The computer system 122 may include a processor 124 and at least one memory 126 that may be part of the processor 124 or a separate data storage device. The memory 126 may store a digital, electronic or computer readable representation 128 of the component 102. The memory 126 may store digital representations of any component, part or other workpiece that may be inspected by the system 100. The digital representation 128 may be a computer assisted design (CAD) representation of the component 102 or similar digital, electronic or computer readable representation of the component 102.

The processor 124 or memory 126 may also include a computer program, software or data structure 130 to transform pixel coordinates of an x-ray image of any defects in the component into coordinates for point locations on the x-ray detection panel 110 corresponding to any defects. The processor 124 or memory 126 may also include another computer program, software or data structure 132 to translate point locations on the x-ray detection panel 110 to coordinates in the digital representation 128 of the component 102.

The computer system 122 may also include a display 134 and input and output devices 136 to provide an operator interface for control and operation of the system 100. An x-ray image 138 or images of the component 102 may be displayed on the display 134. The input/output devices 136 may include a keyboard, point device or mouse, printer or similar input/output devices.

The system 100 may also include a marking device 138 to mark a location of any defects found in the component 102 during an inspection process. The marking device 138 may be an engraving tool, pen or ink dispenser or similar device to put a visible or identifiable mark on the component 102 indicating a location of any defects so that they may be repaired. The marking device 138 may be connected to a marking robot 140 or similar device. The marking device 138 and marking robot 140 may be connected to the computer system 122 to control operation and movement of the marking robot 140 and marking device 138 for precise marking or indication of any defects in the component 102. The coordinates of any defects in the digital representation 128 of the component 102 may be used to control the movement and operation of the marking robot 140 and marking device 138.

The system 100 of the present invention may also be used to detect trends to determine if there may be a problem with a manufacturing process or machine. The memory 126 may store the results of inspections of different components that may be compared statistically or by other means to determine if the same flaws or defects may be reoccurring in a particular type component. The inspection results may then be studied or compared to determine if there may be a problem with the manufacturing process or with a particular machine or apparatus in the manufacturing process.

Figure 2:
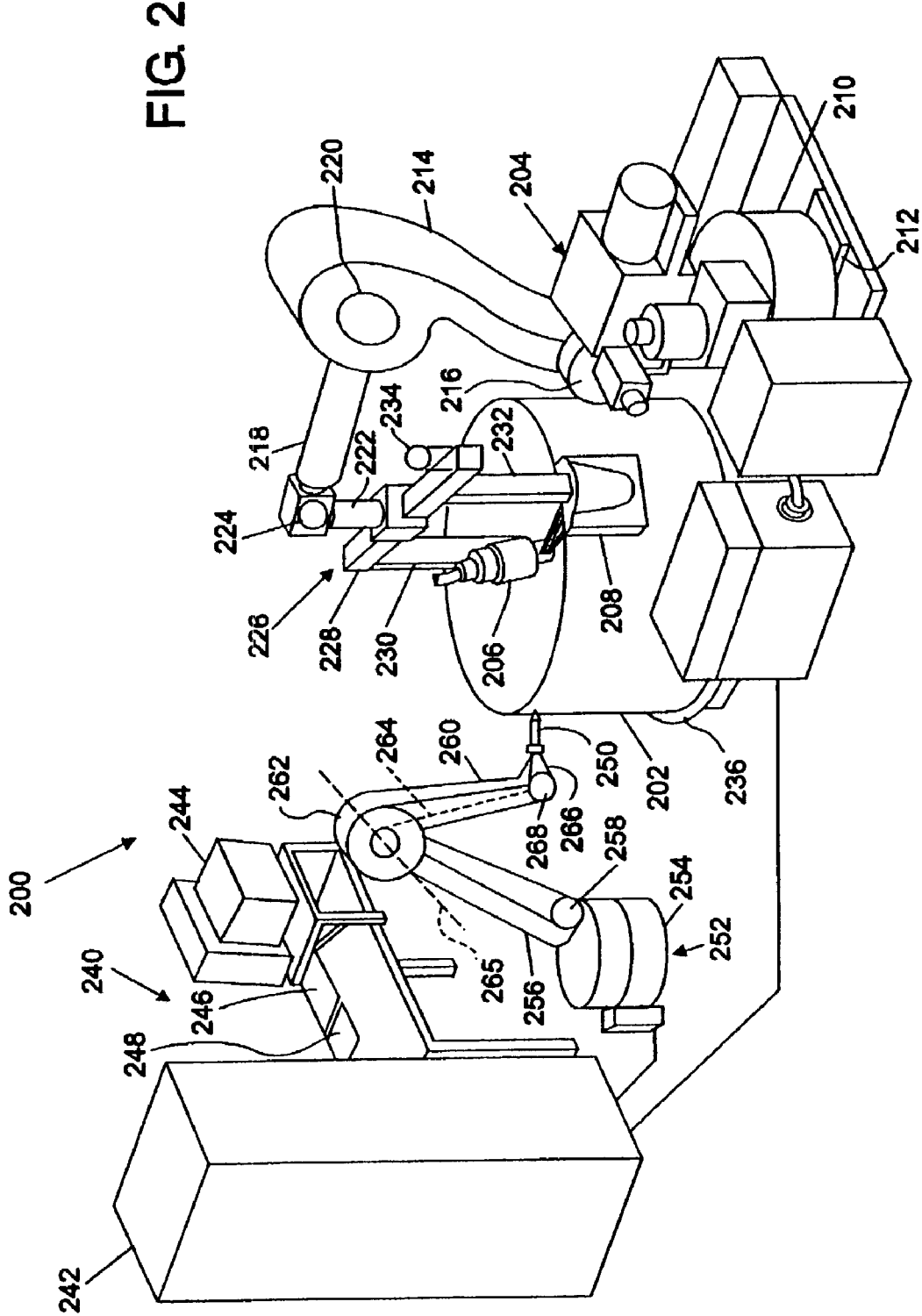
FIG. 2 is an illustration of an exemplary system to inspect a component in accordance with an embodiment of the present invention.

FIG. 2 is an illustration of an exemplary system 200 to inspect a component 202 in accordance with an embodiment of the present invention. The system 200 may be used for the system 100 in FIG. 1. The system 200 may also include a robot 204 or the like to hold and manipulate an x-ray source 206 and x-ray detector 208. The robot 204 may include a base 210. The base 210 may pivot to rotate the base 210 and robot 204 about an axis that may extend vertically from the base 210. The base 210 may also be mounted on a track 212 to permit the base 210 and robot 204 to move laterally toward or away from the component 202.

The robot 204 may include a first articulating arm 214 that may be coupled to the base 210 by a first joint 216 or pivot point. The first joint 216 may permit the first articulating arm 214 to move, rotate or tilt relative to the base 210. The robot 204 may include a second articulating arm 218 that be coupled to the first articulating arm 214 by a second joint 220 or pivot point. The second joint 220 may permit the second articulating arm 218 to move or rotate relative to the first articulating arm 214. A third articulating arm 222 may be coupled to the second articulating arm 218 by a third joint 224 or pivot point. The third articulating arm 222 may move or rotate relative to the second articulating arm 218. The first, second and third articulating arms 214, 218 and 222 may all be rotated relative to one another to precisely control the positioning of the x-ray source 206 and x-ray detector 208 relative to the component 202.

The third articulating arm 222 may be connected to a slide bar assembly 226 or the like. The slide bar assembly 226 may be used for the slide bar assembly 114 in FIG. 1. The slide bar assembly 226 may include a support assembly 228 or linear axis assembly and a first support arm 230 and a second support arm 232 may each be movably coupled to the support assembly 228. The x-ray source 206 may be coupled to the first support arm 230 and the x-ray detector 208 may be coupled to the second support arm 232. The support assembly 228 may include a motorized mechanism 234 to move the first support arm 230 and the second support arm 232 toward or away from each other equal distances. Accordingly, the x-ray source 206 and the x-ray detector 208 may be moved toward or away from one another and the component 202 equal distances, so that proper images of the component 202 may be viewed or acquired as part of an inspection process. The support assembly 228 may include a series of belts and pulleys (not shown) driven by the motorized mechanism 234 to move the first and second arms 230 and 232 toward or away from each other with the x-ray source 206 and x-ray detector 208 attached respectively thereto. Alternatively, the first and second arms 230 and 232 may be coupled to respective screws in the support assembly 228. The screws may be turned by the motorized mechanism 234 or the like to move the arms 230 and 232 along the screws toward or away from one another depending upon which way the screws are turned. One screw may be a right-hand thread and the other a left-hand thread and may be operated by a single motorized mechanism, such as motorized mechanism 234, or multiple motorized mechanisms.

The system 200 may also include a rotary table 236 or the like on which the component 202 may be placed or fixtured for inspection. The rotary table 236 may rotate the component 202 to inspect different portions of the component 202 and to register or zero an axis or origin of the component 202 with an axis or origin of the system 200.

The system 200 may also include a computer system 240 to control operation of the system 200. The computer system 240 may be substantially the same as the computer system 122 in FIG. 1. The computer system 240 may include a processor 242 including a memory or data storage devices (not shown in FIG. 2). The computer system 240 may also include a display 244 and input/output device, such as a keyboard 246 and pointing device 248 or mouse.

The system 200 may also include a marking device 250 to mark any flaws or defects on the surface of the component 202. The marking device 250 may be the same as the marking device 138 in FIG. 1. The marking device 250 may be manipulated by a marking robot 252. The marking robot 252 may include a base 254 that may rotate to position the marking device 250 relative to the component 202. A first articulating arm 256 may be pivotally coupled to the base 254 by a first joint 258 or pivot point that permits the first articulating arm 256 to pivot relative to the base 254. A second articulating arm 260 may be pivotally coupled to the first articulating arm 256 by a second joint 262 or pivot point that permits the second articulating arm 260 to pivot relative to the first articulating arm 256. The second articulating arm 260 may be able to rotate about an axis 264 that is perpendicular to an axis 265 of the second joint 262. The second articulating arm 260 may then rotate relative to the second joint 262 for positioning of the marking device 250. A marking head 266 for mounting the marking device 250 to the marking robot 252 may be pivotally coupled to the second articulating arm 260 by a third joint 268 or pivot point. The marking device 250 may be mounted to the marking head 266 in a selected offset to cause a substantially circular pattern to be inscribed around any defects in the component 202. As previously described, movement and positioning of the marking device 250 by the marking robot 252 may be controlled by the computer system 240 using the coordinates of any defects from the x-ray image that have been translated or transformed to coordinates in the digital representation of the component 202.

Figure 3B:
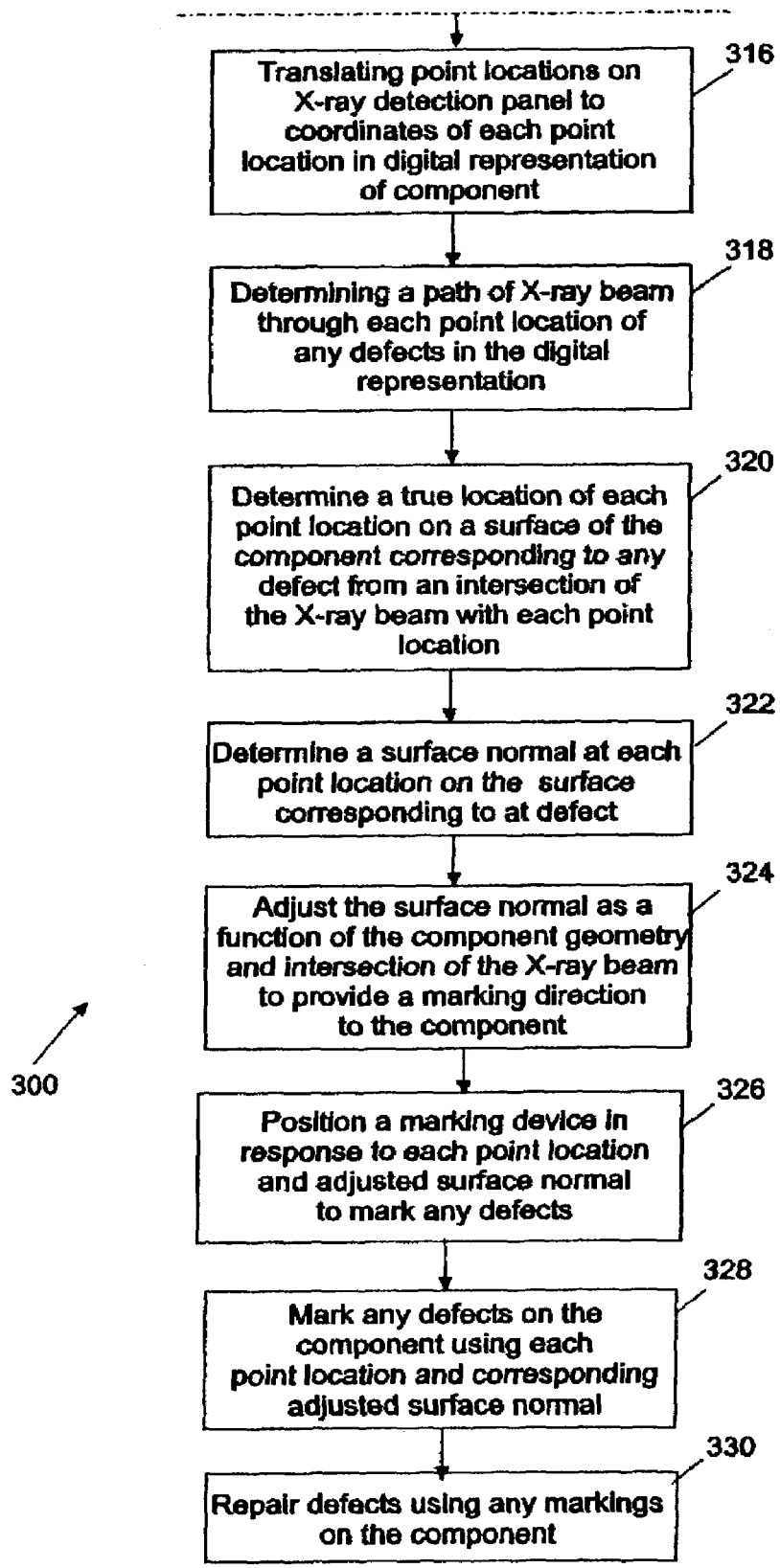

FIGS. 3A and 3B are a flow chart of a method 300 of inspecting a component, in accordance with an embodiment of the present invention. The method 300 may be implemented by the inspection system 100 of FIG. 1 or 200 of FIG. 2. In block 302, a component, such as component 102 (FIG. 1), 202 (FIG. 2) or other component, part or workpiece, may be mounted to a rotary table similar to the rotary table 236 of FIG. 2 or mounted to some other fixturing device. In block 304, the registration or zeroing of the component to be inspected with the axes of the inspection system may be performed. A three-dimensional digital, electronic or computer readable representation of the component to be inspected may be acquired in block 306. As previously discussed, the digital representation may be a three-dimensional CAD representation or the like of the component. The digital representation of the component to be inspected may have been previously acquired and stored in a memory of the computer system of the inspection system as previously described. In block 308, the geometry of the component may be translated to coordinate with the geometry of the inspection system. Any offsets due to fixturing or other reasons may be taken into account so that the axes of the component may be coordinated with the axes of the inspection system. In block 310, the component registered with the inspection system may be rotated a predetermined angle "a" by the rotary table to register a center point "C" of an x-ray beam relative to an axis of the registered component. In block 312, the x-ray source may be activated and an x-ray image of the component may be acquired.

Figure 4:
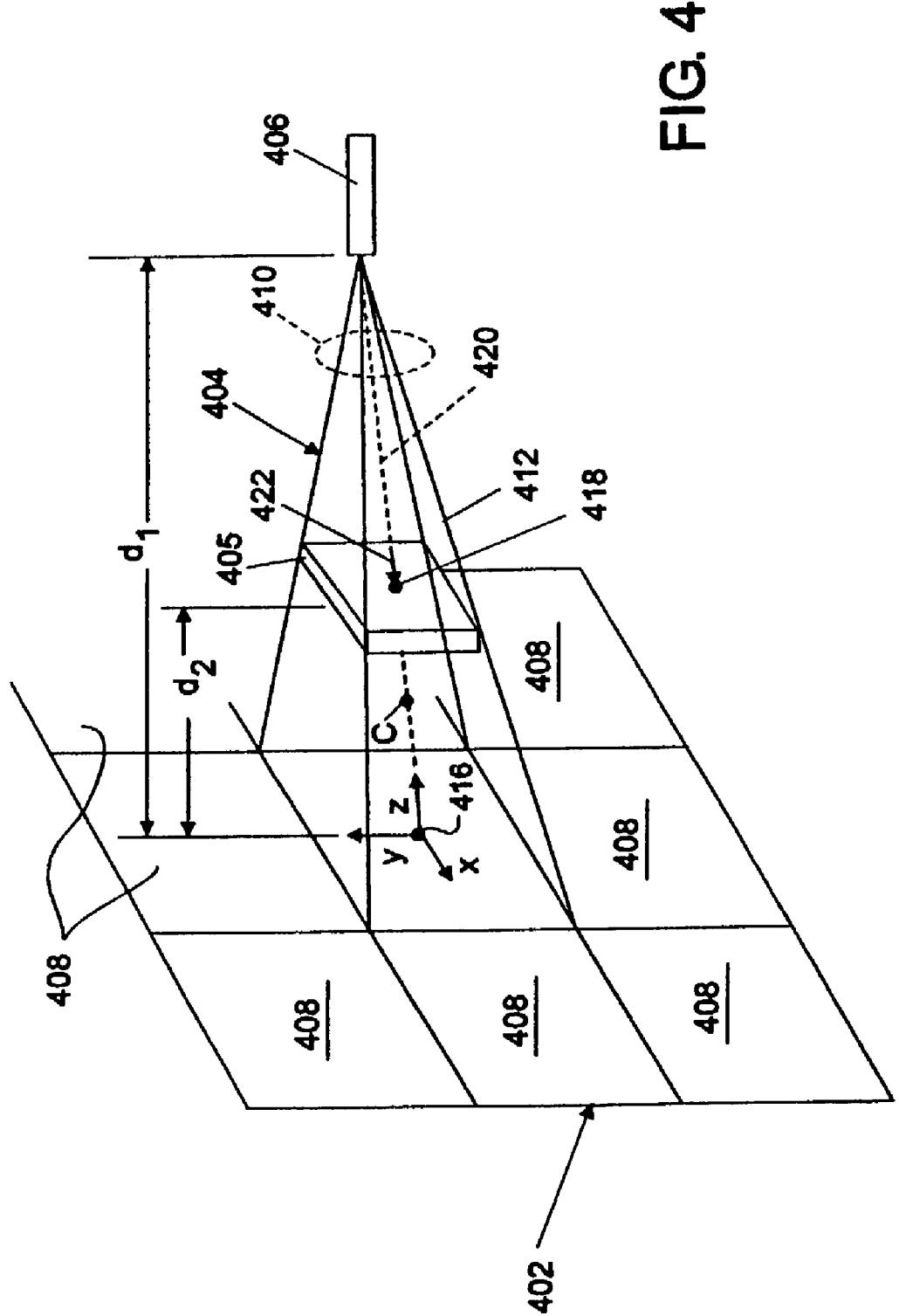
FIG. 4 is a partial view of an x-ray detection panel with an x-ray beam incident on a component under inspection disposed between the x-ray detection panel and a source.

In block 314, coordinates of pixels in an x-ray image that indicate any defects in the component may be translated or transformed into coordinates for point locations on an x-ray detection panel corresponding to any defects. Referring also to FIG. 4, FIG. 4 is a partial view of an x-ray detection panel 402 with an x-ray beam 404 incident on the panel 402, through an component 405 under inspection, from an x-ray source 406. The x-ray detection panel 402 may be the same as the panel 110 in FIG. 1. The x-ray detection panel 402 may be thought of as being divided into different portions 408. Each portion 408 may correspond to a pixel in the x-ray image. The different portions 408 or pixels of the x-ray detection panel 402 may be substantially square or rectangular. The different portions 408 are shown in FIG. 4 to be much larger than actuality for purposes of explanation. Each portion 408 may basically be pinpoints or point locations on the x-ray detection panel 402. Because the dimensions of the x-ray image are known relative to the x-ray detection panel 402, the coordinates of pixels in the x-ray image may correspond to coordinates for portions 408 or point locations on the detection panel 402. Accordingly, coordinates of pixels in the x-ray image that indicate any defects may be transformed into coordinates for corresponding point locations or portions 408 on the x-ray detection panel 402.

In block 316 of FIG. 3, coordinates for point locations on the x-ray detection panel 402 may be transformed or translated to corresponding coordinates of each point location in the three-dimensional digital representation of the component 405. Referring back to FIG. 4, the x-ray beam 404 may be thought of as being divided into multiple segments 410. Each segment 410 of the x-ray beam 404 may form an x-ray beam pyramid 412 with a corresponding portion 408 or pixel of the x-ray detection panel 402 as the base of the pyramid 410. Only a single x-ray beam pyramid 412 is shown in FIG. 4 for clarity. The distance d1 between the x-ray source and the panel 402 may be determined and stored in the inspection system. The distance d2 between the detection panel 402 and a component 405 or section of the component 405 through which the x-ray beam pyramid 412 passes may also be determined and stored in the inspection system. Because the distances d1 and d2 are known and because the position of the rotary table or fixture is known with respect to the coordinates of the inspection system, a point location 416 on the detection panel 402 may be transferred to a point location 418 on the actual component 405. Further, because the geometry of the component 405 is coordinated with the geometry of the inspection system in block 308, the point location 418 on the component 405 may be translated to a point location in the digital representation of the component 405. Accordingly, all point locations on the x-ray detection panel 402 that indicate a defect may be translated to coordinates in the digital representation of the component 405.

In block 318 of FIG. 3, a path 420 (FIG. 4) of the x-ray beam 404 through each point location 418 of any defects in the digital representation of the component 405 may be determined. Because the location of the x-ray beam pyramid 412 and the location of the component 405 are known in the coordinate system of the inspection system, the path 420 of the x-ray beam 404 through each point location 418 of any defects can be determined in the digital representation of the component 405. In block 320 of FIG. 3B, a true location of each point location 418 on a surface of the component 405 corresponding to any defects may be determined from an intersection of the path 420 of the x-ray beam 404 with each point location 418. An operator may locate a flaw or defect by placing a cursor or other indicator on the defect in a digital image of the component 405 on a display, such as the display 134 in FIG. 1. The operation may use an input device, such as the input device 136 of the computer system 122 of FIG. 1, to place the cursor on the defect in the digital image of the component 405. The computer system associated with the inspection system may then translate the pixel location of the cursor to point locations on the detection panel 402 and in the digital representation of the component 405 to provide a true location corresponding to any defects on the surface of the component 405 in the digital representation of the component 405.

In block 322, a surface normal 422 at each point location 418 or true location on the surface of component 405 corresponding to a defect may be determined. The surface normal 422 may be determined from the path 420 of the x-ray beam 404 at the point location 418 in the digital representation of the component 405. In block 324, the surface normal 422 may be adjusted as a function of the component geometry and intersection of the x-ray beam 404 to provide a safe marking direction for a marking device to the component 405. The marking device may be marking device 250 of FIG. 2. In block 326, the marking device may be positioned in response to each point location 418 or true location and adjusted surface normal 422 as defined in the digital representation of the component 405 to mark any defects on a surface of the component 405. In block 328, any defects may be marked on the component 405 using each point location 418 and corresponding adjusted surface normal 422. A predetermined pattern may be applied to the component 405 by the marking device in block 328. In block 330, the markings on the component may be used to repair any defects. In an alternate embodiment, the component 405 may be automatically repaired using the coordinates in the digital representation of the component 405 that correspond to any defect. For example, the component 405 may be repaired by removing the defect, such as by drilling or other means, using the digital representation. The removed volume of material may then be replaced by depositing material, such as weld material or the like, using the digital representation.

Although specific embodiments have been illustrated and described herein, those of ordinary skill in the art appreciate that any arrangement which is calculated to achieve the same purpose may be substituted for the specific embodiments shown and that the invention has other applications in other environments. While the present invention has been described with respect to an x-ray inspection system, the present invention has applicability to other systems where an image of the component may be obtained and pixel locations on the image may be translated or transformed to coordinates in a digital representation of the component. This application is intended to cover any adaptations or variations of the present invention. The following claims are in no way intended to limit the scope of the invention to the specific embodiments described herein.

The invention claimed is:

1. A method to inspect a component, comprising:
   transforming coordinates of pixels on an x-ray image of the component that indicate any defects in the component to coordinates in a three dimensional digital representation of the component;
   marking the component using the coordinates in the digital representation to identify locations of any defects and using a marking device mounted to a robot; and
   controlling operation of the robot using the coordinates in the digital representation of the component of locations of any defects.

2. The method of claim 1, further comprising transferring coordinates of any pixels on the x-ray image that indicate defects in the component into point locations on an x-ray detection panel.

3. The method of claim 2, further comprising translating point locations on the x-ray detection panel that correspond to any defects to coordinates of each point location in the digital representation of the component.

4. The method of claim 3, further comprising determining a path of an x-ray beam through each point location of any defects in the digital representation.

5. The method of claim 4, further comprising determining a true location of each point location on a surface of the component corresponding to any defect from an intersection of the x-ray beam with each point location.

6. The method of claim 5, further comprising determining a surface normal at each point location on the surface corresponding to a defect.

7. The method of claim 6, further comprising adjusting the surface normal as a function of the component geometry and intersection of the x-ray beam to provide a marking direction to the component.

8. The method of claim 7, further comprising using each point location and corresponding adjusted surface normal to mark any defects on the surface of the component.

9. The method of claim 8, further comprising positioning a marking device in response to each point location and corresponding adjusted surface normal to mark any defects.

10. The method of claim 1, further comprising positioning a marking device in response to the coordinates in the digital representation of the component.

11. A method to inspect a component, comprising:
    transforming coordinates of pixels on an x-ray image of the component that indicate any defects in the component to coordinates in a digital representation of the component;
    marking the component using the coordinates in the digital representation to identify locations of any defects; and
    mounting an engraving head offset from a gripper axis to inscribe a circle about each point when the gripper axis is rotated.

12. A method to inspect a component, comprising:
    determining coordinates defining any defects in the component on an x-ray detection panel;
    transforming the coordinates defining any defects on the x-ray detection panel to locations on the component;
    marking a surface of the component corresponding to the locations on the component of any defects using a three dimensional digital representation of the component and using a marking device mounted to a robot; and
    controlling operation of the robot using the digital representation of locations on the component of any defects.

13. The method of claim 12, wherein determining coordinates defining any defects comprises transferring coordinates of pixels on an x-ray image of the component that indicate any defects into point locations on the x-ray detection panel corresponding to any defects.

14. The method of claim 13, further comprising translating point locations on the x-ray detection panel to coordinates in the digital representation of the component for each point location of any defects.

15. The method of claim 14, further comprising determining a path of the x-ray beam through each point location of any defects.

16. The method of claim 15, further comprising determining a true location of each point location on a surface of the component corresponding to any defect from an intersection of the x-ray beam with each point.

17. The method of claim 16, further comprising determining a surface normal at each point on the surface corresponding to any defect.

18. The method of claim 17, further comprising adjusting the surface normal as a function of the component geometry and intersection of the x-ray beam to provide a safe making direction to the component.

19. The method of claim 18, further comprising marking the surface of the component at each point corresponding to the locations of any defects.

20. The method of claim 12, further comprising automatically repairing the component using a digital representation of the component.

21. A system to inspect a component, comprising:
an x-ray source to direct an x-ray beam through the component;
an x-ray detector to detect the x-ray beam after passing through the component, wherein the x-ray detector includes an x-ray detection panel;
a processor to transform coordinates on the x-ray detection panel that detect any defects to a three dimensional digital representation of locations on the component of any defects; and
a marking device mounted on a robot to mark the component to identify locations of any defects, wherein the robot is controlled using the digital representation of locations on the component of any defects.

22. The system of claim 21, further comprising a data structure to transfer coordinates on an x-ray image of the component that indicate any defects into point locations on the x-ray detection panel.

23. The system of claim 22, further comprising another data structure to translate point locations on the x-ray detection panel to coordinates in a digital representation of the component for each point corresponding to a location of any defects.

24. The system of claim 21 further comprising another robot on which the x-ray source and x-ray detector are mounted and movable relative to one another.

25. A system to inspect a component, comprising:
an x-ray source to direct an x-ray beam through the component;
an x-ray detector to detect the x-ray beam after passing through the component, wherein the x-ray detector includes an x-ray detection panel;
a robot on which the x-ray source and x-ray detector are mounted and movable relative to one another;
a processor to transform coordinates on the x-ray detection panel that detect any defects to a digital representation of locations on the component of any defects;
another robot; and
a marking device mounted on the other robot to mark the component to identify locations of any defects, wherein the other robot is controlled using the digital representation of locations on the component of any defects.

26. A system to inspect a component, comprising:
an x-ray source to direct an x-ray beam through the component;
an x-ray detector to detect the x-ray beam after passing through the component;
a display to display an x-ray image of the component in response to passing the x-ray beam through the component;
a three dimensional digital representation of the component;
a processor;
a data structure to operate on the processor to transform coordinates of pixels on the x-ray image of the component that indicate any defects to coordinates in the digital representation of the component;
a robot; and
a marking device mounted to the robot to mark the component using the coordinates in the digital representation to identify locations of any defects, wherein the robot is controlled using the digital representation of locations on the component of any defects.

27. The system of claim 26, further comprising another data structure to operate on the processor to transfer coordinates of any pixels on the x-ray image that indicate any defects in the component into point locations on an x-ray detection panel of the x-ray detector.

28. The system of claim 27, further comprising a further data structure to operate on the processor to translate the point locations on the x-ray detection panel that correspond to any defects to coordinates of each point location in the digital representation of the component.

29. The system of claim 26, further comprising an x-ray system robot, wherein the x-ray source and the x-ray detector are mounted on the x-ray system robot and movable relative to one another.

30. The system of claim 26, wherein the marking device comprises an engraving tool.

31. A system to inspect a component, comprising:
an x-ray source to direct an x-ray beam through the component;
an x-ray detector to detect the x-ray beam after passing through the component;
an x-ray system robot, wherein the x-ray source and the x-ray detector are mounted on the x-ray system robot and movable relative to one another;
a display to display an x-ray image of the component in response to passing the x-ray beam through the component;
a digital representation of the component;
a processor;
a data structure to operate on the processor to transform coordinates of pixels on the x-ray image of the component that indicate any defects to coordinates in the digital representation of the component;
a marking device to mark the component using the coordinates in the digital representation to identify locations of any defects; and
a marking robot, wherein the marking device is mounted to the marking robot and operation of the marking robot is controlled using the coordinates in the digital representation of the component of any defects.

32. The system of claim 31, further comprising a rotary table to mount the component, wherein the rotary table moves the component relative to the x-ray source and detector to register the component with respect to a coordinate system of the x-ray robot and the marking robot.

* * * * *